(12) United States Patent
Nijhawan et al.

(10) Patent No.: US 10,771,727 B2
(45) Date of Patent: Sep. 8, 2020

(54) MONITORING SYSTEM WITH HEADS-UP DISPLAY

(71) Applicant: Vital Optics, Inc, San Jose, CA (US)

(72) Inventors: Sumit Nijhawan, San Jose, CA (US); Jeffrey Nguyen, Irvine, CA (US); Defeng Xu, Los Angeles, CA (US)

(*) Notice: Subject to any disclaimer, the term of this patent is extended or adjusted under 35 U.S.C. 154(b) by 16 days.

(21) Appl. No.: 15/965,290

(22) Filed: Apr. 27, 2018

(65) Prior Publication Data
US 2019/0335131 A1    Oct. 31, 2019

(51) Int. Cl.
| | |
|---|---|
| H04N 5/44 | (2011.01) |
| H04N 5/64 | (2006.01) |
| H04N 5/38 | (2006.01) |
| H04N 7/10 | (2006.01) |
| G02B 27/01 | (2006.01) |
| G06F 3/16 | (2006.01) |
| H04N 5/57 | (2006.01) |
| H04N 7/01 | (2006.01) |
| G16H 50/20 | (2018.01) |
| G06F 3/01 | (2006.01) |

(52) U.S. Cl.
CPC .......... *H04N 5/44* (2013.01); *G02B 27/0172* (2013.01); *H04N 5/38* (2013.01); *H04N 5/64* (2013.01); *H04N 7/10* (2013.01); *G02B 2027/0178* (2013.01); *G06F 3/017* (2013.01); *G06F 3/167* (2013.01); *G16H 50/20* (2018.01); *H04N 5/57* (2013.01); *H04N 7/01* (2013.01)

(58) Field of Classification Search
None
See application file for complete search history.

(56) References Cited

U.S. PATENT DOCUMENTS

| | | | |
|---|---|---|---|
| 6,847,336 B1 | 1/2005 | Lemelson et al. | |
| 9,581,822 B2 | 2/2017 | Morimoto | |
| 2011/0282130 A1* | 11/2011 | Krueger | G02B 27/017 600/27 |
| 2012/0062445 A1* | 3/2012 | Haddick | H04N 5/23293 345/8 |
| 2013/0021373 A1* | 1/2013 | Vaught | G06F 3/013 345/633 |

(Continued)

FOREIGN PATENT DOCUMENTS

| | | |
|---|---|---|
| DE | 10 2008 063 822 B4 | 5/2013 |
| GB | 2543277 A | 4/2017 |

OTHER PUBLICATIONS

Drake-Brockman et al., "Patient monitoring with Google Glass: a pilot study of a novel monitoring technology", Pediatric Anesthesia, 26, pp. 539-546, Mar. 19, 2016. (Year: 2016).*

(Continued)

*Primary Examiner* — Reza Aghevli
(74) *Attorney, Agent, or Firm* — Arnold & Porter Kaye Scholer LLP

(57) ABSTRACT

A monitoring system having a heads-up display may include a receiver, a transmitter, and a monitor device. The monitoring system may be designed to display video information in a peripheral field and may be designed to display real-time information while minimizing latency. The monitoring system may provide for the monitoring or recording of patient vital information by a healthcare professional performing medical tasks.

14 Claims, 9 Drawing Sheets

(56) References Cited

U.S. PATENT DOCUMENTS

| | | | |
|---|---|---|---|
| 2014/0152792 A1* | 6/2014 | Krueger | G06K 9/00604 348/78 |
| 2015/0015458 A1* | 1/2015 | Cho | G06F 3/011 345/8 |
| 2015/0070389 A1* | 3/2015 | Goto | G06T 7/00 345/633 |
| 2015/0135209 A1* | 5/2015 | LaBosco | H04N 21/43635 725/31 |
| 2016/0110921 A1* | 4/2016 | Takahashi | G09G 3/003 345/633 |
| 2016/0162012 A1* | 6/2016 | Chang | G06F 1/3265 345/211 |
| 2017/0077738 A1* | 3/2017 | Park | H02J 7/025 |
| 2017/0115839 A1* | 4/2017 | Park | G06F 3/017 |
| 2017/0185716 A1 | 6/2017 | Rodriguez et al. | |
| 2018/0132550 A1* | 5/2018 | Czajka | A41D 13/1209 |
| 2018/0172996 A1* | 6/2018 | Inman | G02C 7/104 |
| 2018/0249087 A1* | 8/2018 | Arnold | A41D 27/205 |
| 2018/0348863 A1* | 12/2018 | Aimone | A61B 5/0476 |
| 2019/0018238 A1* | 1/2019 | Jenson | G03B 21/62 |
| 2019/0027113 A1* | 1/2019 | Kaine | G06F 3/0308 |
| 2019/0086920 A1* | 3/2019 | Miller | B64D 17/80 |
| 2019/0227311 A1* | 7/2019 | Nair | G02B 27/017 |

OTHER PUBLICATIONS

Liebert et al., "Novel Use of Google Glass for Procedural Wireless Vital Sign Monitoring," *Surgical Innovation*, 23(4):366-373 (2016).

Liu et al., "Clinical Implementation of a Head-Mounted Display of Patient Vital Signs," 13th IEEE International Symposium on Wearable Computers, Linz, Austria, pp. 47-54 (2009).

Vorraber et al., "Medical Applications of Near-Eye Display Devices: An Exploratory Study," *Int'l J. Surg.*, 12:1266-1272 (2014).

Drake-Brockman, T.F.E., Datta, A. and von, Ungern-Sternberg, B.S. (Mar. 19, 2016), Patient monitoring with Google Glass: a pilot study of a novel monitoring technology. Paediatric Anaesthesia, 26: 539-546. doi:10.1111/pan.12879.†

\* cited by examiner
† cited by third party

MONITORING SYSTEM WITH HEADS-UP DISPLAY

FIELD OF THE INVENTION

The present invention relates generally to a monitoring system having a heads-up display. The system may, for example, provide for the monitoring or recording of patient vital information by a healthcare professional performing medical tasks.

BACKGROUND OF THE INVENTION

A healthcare provider that performs a medical procedure often needs to monitor a patient's vital information or "vital signs" simultaneously. The need to monitor vital information is of particular importance during surgical procedures when general anesthesia is provided to a patient. Viewing a patient's vital information may indicate to a healthcare provider that the patient is experiencing an adverse event such as an oxygen desaturation, interruption of breathing due to obstruction or lack of effort, myocardial infarction, sudden change in blood pressure or another multitude of medical emergencies. Often times a healthcare provider that provides anesthesia, and thus must monitor a patient's vital information, is the same healthcare provider that performs a medical or surgical procedure. In such situations, the healthcare provider is often required to shift his or her attention away from the patient in order to view vital information on the display of a monitor device while the procedure is being performed. Such an occurrence can cause the healthcare provider's attention and focus to be diverted from the patient, resulting in an unreasonable and potentially dangerous situation. Furthermore, a healthcare professional that performs a medical procedure without a simultaneous view of a patient's vital information may be delayed in responding to the emergency or adverse event.

There exists a need to provide healthcare professionals with a more safe and convenient way to monitor a patient's vital information while attentively performing a medical procedure, thereby improving patient outcomes. Moreover, there exists a need to provide real-time monitoring capability that does not unnecessarily interfere with the performance of medical procedures.

SUMMARY OF THE INVENTION

This patent document discloses a monitoring system having a heads-up display for displaying video information, thereby eliminating the need for a user to directly view a monitor device. The monitoring system is particularly useful for healthcare providers with a need to view a patient's vital information during the course of a medical or surgical procedure. Such healthcare providers include oral and maxillofacial surgeons, anesthesiologists, dental anesthesiologists, dentists, post-anesthesia care unit (PACU) personnel, critical care monitoring personnel, nurses, and emergency department (ED) physicians. The monitoring system allows a healthcare provider to focus on a medical procedure while simultaneously monitoring a patient's vital information via a heads-up display device. The monitoring system can be used in an operating room, where an anesthesiologist can move freely about the room or the patient, while continuously monitoring vital information. The monitoring system can also be used by ED physicians performing procedures while a patient is sedated. The monitoring system may be particularly useful, for example, when a separate dedicated practitioner is not available to monitor the anesthesia, or for a practitioner that may want to monitor patient status from a remote location, or move freely about the surgical suite while real-time monitoring the patient's vital signs.

According to an embodiment, a monitoring system includes a heads-up display device. The heads-up display device may include at least one safety lens, may include an LCOS display, and may include a brightness and/or contrast controller. The heads-up display device may lack a CPU or an operating system. The heads-up display device may be configured to display information only in a peripheral field of vision.

The monitoring system may include a receiver configured to receive a video signal. The receiver may provide video information and power to the heads-up display device via a cable connecting the receiver to the heads-up display device. Such video information may be HDMI video information. The receiver may be portable, may be wearable, and may include a belt clip. The receiver may be detachably connected to the heads-up display device.

The monitoring system may include a transmitter for wirelessly transmitting a video signal to the receiver. The transmitter may be configured to receive VGA video information and HDMI video information. The monitoring system may include a monitor device for providing video information to the transmitter. The monitor device may serve as a blood pressure monitor, a heart rate monitor, an electrocardiograph, a respiratory monitor, a capnograph, or a pulse oximeter. The monitoring system may include a converter for converting video information from the monitor device to a format, such as HDMI.

The monitoring system may include a plurality of heads-up display devices, each heads-up display device associate with one of a plurality of receivers. The monitoring system may be responsive to voice commands and may be responsive to gesture commands.

BRIEF DESCRIPTION OF THE DRAWINGS

The accompanying drawings, which are included as part of the present specification, illustrate the presently preferred embodiments and, together with the general description given above and the detailed description given below, serve to explain and teach the principles of the monitoring system described herein.

Figure 1:
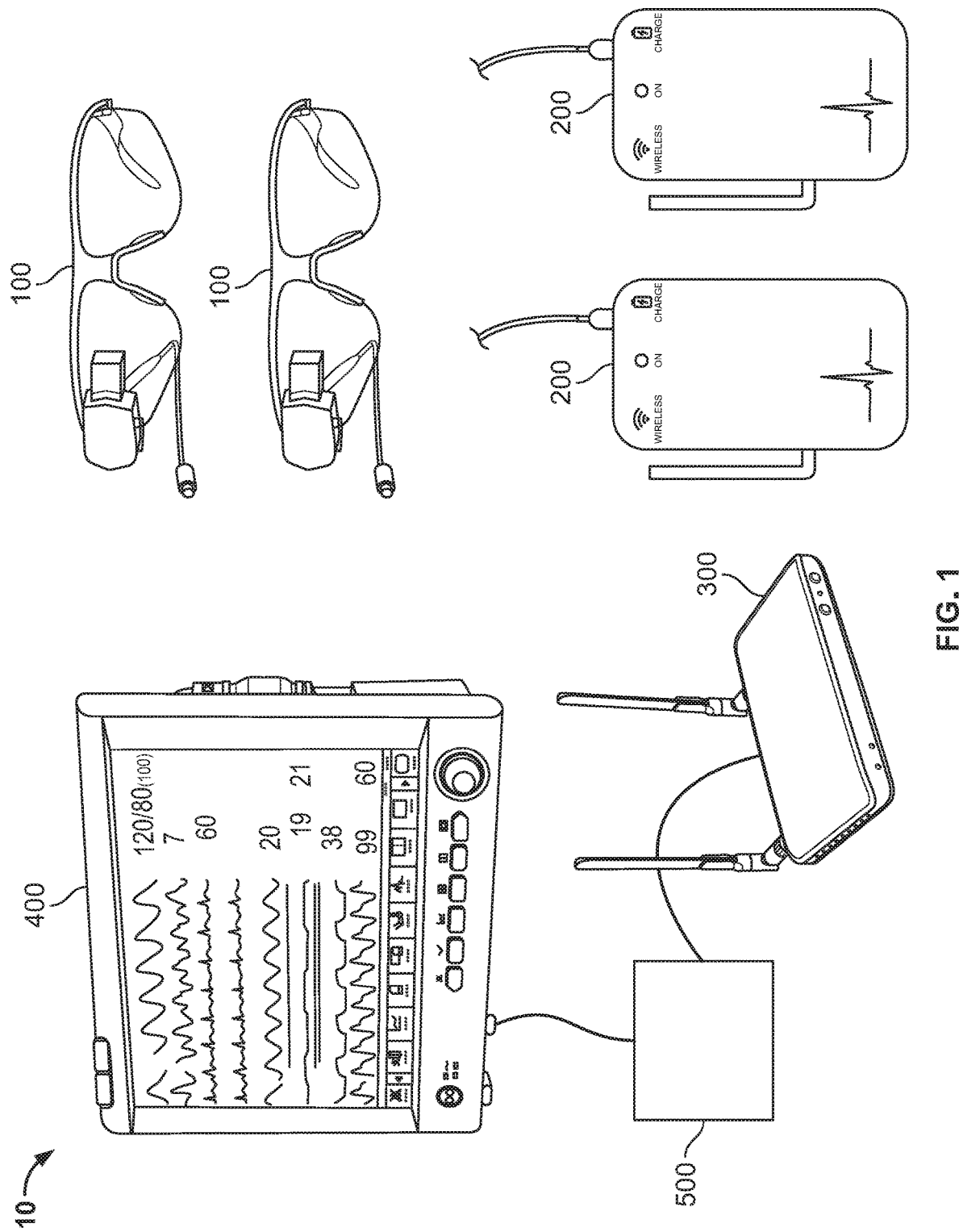
FIG. 1 shows a monitoring system in accordance with an embodiment of the invention.

The figures are not necessarily drawn to scale and the elements of similar structures or functions are generally represented by like reference numerals for illustrative purposes throughout the figures. The figures are only intended to facilitate the description of the various embodiments described herein; the figures do not describe every aspect of the teachings disclosed herein and do not limit the scope of the claims.

DETAILED DESCRIPTION OF THE INVENTION

The following description is presented to enable any person skilled in the art to create and use a monitoring system in accordance with the present invention. Each of the features and teachings disclosed herein can be utilized separately or in conjunction with other features to implement the disclosed system and method. Representative examples utilizing many of these additional features and teachings, both separately and in combination, are described in further detail with reference to the attached drawings. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense, and are instead taught merely to describe particularly representative examples of the present teachings.

In the following description, for purposes of explanation only, specific nomenclature is set forth to provide a thorough understanding of the present teachings. However, it will be apparent to one skilled in the art that these specific details are not required to practice the present teachings.

Referring first to FIG. 1, a monitoring system 10 is shown in accordance with an exemplary embodiment of the invention. The monitoring system 10 may include one or more heads-up display devices 100, one or more wireless receivers 200, a wireless transmitter 300, a monitor device 400, and a converter box 500.

Figure 2:
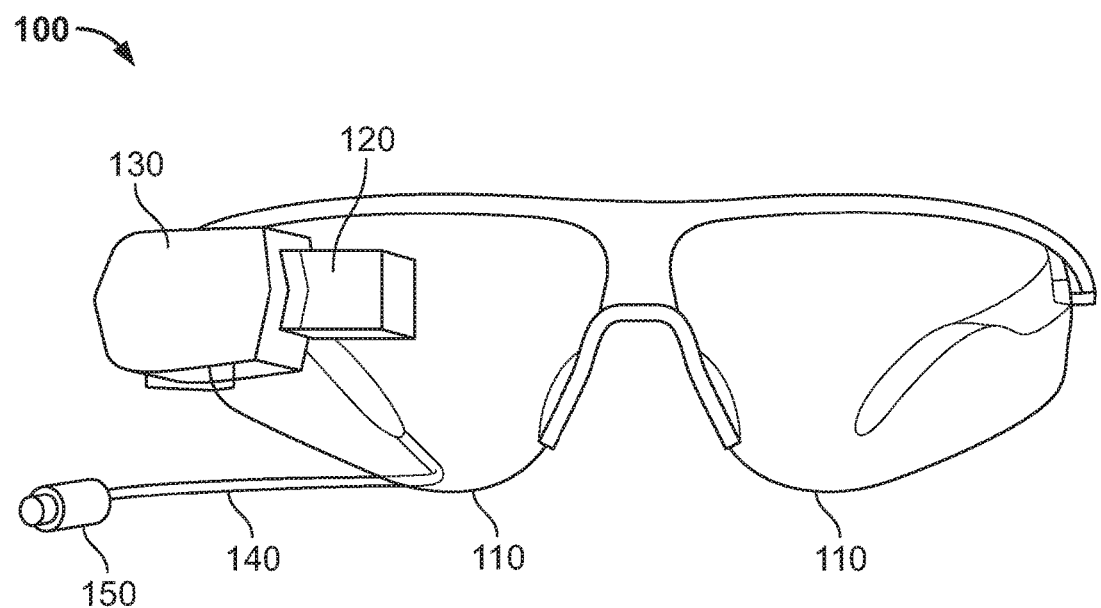
FIG. 2 shows a front view of a heads-up display device in accordance with an embodiment of the invention.
Figure 3:
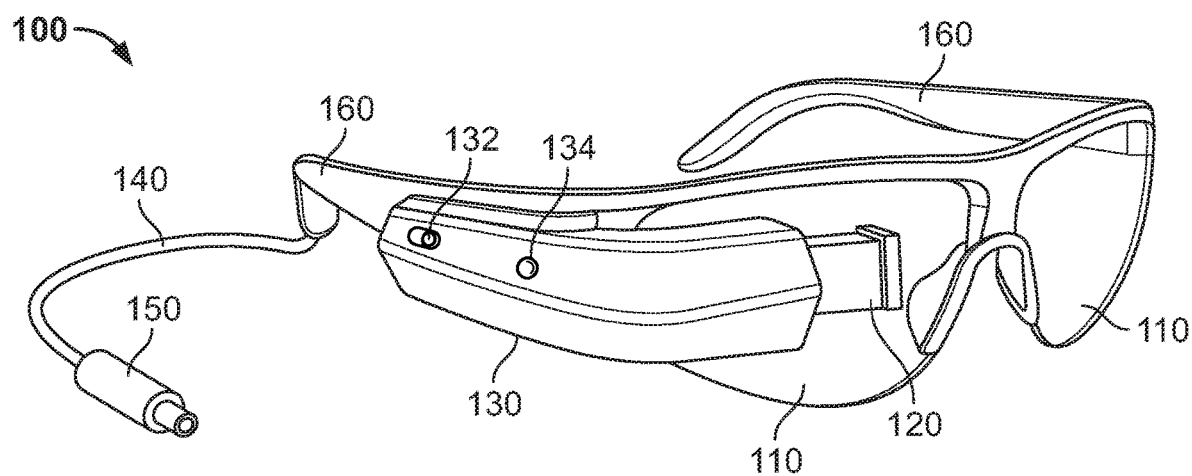
FIG. 3 shows a perspective view of a heads-up display device in accordance with an embodiment of the invention.

Illustrations of an exemplary heads-up display device 100 are provided in FIGS. 2 and 3. The heads-up display device 100 is a head mounted display device that may be worn by a user in a manner similar to that of conventional eyeglasses or goggles. The heads-up display device 100 includes lenses 110, an optical prism 120, a housing 130, and a cable 140 having a connector 150 at its end. Earpieces 160 may be provided to allow a user to wear the heads-up display device 100 in a manner similar to that of conventional eyewear.

The lenses 110 may be formed of any suitable material. The lenses 110 may be formed separately, for example, from two pieces of material to correspond to a user's right and left eyes. Alternatively, the lenses 110 may be formed integrally from a single piece of material. The lenses 110 may serve as safety lenses, providing protection for a user's eyes, and may be formed of a material such that the heads-up display device 100 is ANSI z87.1 rated. The lenses 110 may be prescription lenses, and serve as a substitute for a user's regular prescription eyewear. The heads-up display device 100 may also be designed to be used in conjunction with a user's standard safety glasses or prescription glasses and, thus, may be designed to mount onto a user's standard safety glasses or prescription glasses.

The optical prism 120 serves as a video output device and may display, for example, HDMI video. In an exemplary embodiment, the displayed video may have a resolution of 800×480. The optical sensor 120 may form part of a liquid crystal on silicon (LCOS) display. The optical prism 120 may operate in a manner similar to optical prisms in known devices, such as Google Glass™. Accordingly, the heads-up display device 100 may serve as an augmented reality device. In the embodiment shown in FIG. 1, the optical prism 120 is positioned in the upper lateral portion of the right-side lens 110. The optical prism 120 may, however, be positioned on the upper lateral portion of the left-side lens 110, for example, or in any other position, preferably such that the video output from the optical sensor 120 does not obstruct the user's view through the lenses 110.

In a preferred embodiment, the heads-up display device 100 is configured to display video information only in a user's peripheral field of view. Such a configuration provides an advantage over conventional heads-up display devices in which displayed information may occupy a large portion, or the entirety, of a user's field of view. Information displayed across a large portion of a user's field of view can obstruct the user's view, can be distracting, and can interfere with important tasks. To that end, in an exemplary embodiment, the heads-up display device 100 is configured to only display information in a region that is at an angle of greater than 15° from the center of the heads-up display device 100. In another exemplary embodiment, the heads-up display device 100 is configured to only display information in a region that is at an angle of greater than 30° from the center of the heads-up display device 100. In yet another exemplary embodiment, the heads-up display device 100 is configured to only display information in a region that is at an angle of greater than 45° from the center of the heads-up display device 100. In yet another exemplary embodiment the heads-up display device 100 is configured such that information is only displayed in a single quadrant of the field of view of the heads-up display device 100. For example, information may be displayed only in an upper right quadrant of the field of view, or may be displayed only in an upper left quadrant of the field of view.

The housing 130 contains hardware for displaying video, including, for example, a projector. A controller 132, such as a toggle, button, knob, or switch, may be provided on the housing 130, or elsewhere on the heads-up display device 100, to allow for controlling visual aspects of the display, such as the display brightness. An indicator 134 may also be provided on the housing to indicate, for example, that power is being received by the heads-up display device 100.

While the housing 130 may contain hardware that allows for powering of the display, the housing 130 may be designed without a built-in battery. The absence of a battery inside the housing 130, or elsewhere on the heads-up display device 100, provides advantages over conventional display devices. For example, the absence of a battery in the heads-up display device 100 eliminates the need to refrain from using the heads-up display device 100 while a battery is charging. The absence of a battery also allows the weight of the heads-up display device 100 to be minimized. A battery for powering the heads-up display device 100 may, however, be provided in a receiver 200 as described herein.

The heads-up display device 100 may include a cable 140 for receiving video information to be displayed, and for receiving power to allow for such display. In the exemplary embodiment illustrated in FIGS. 2 and 3, the cable includes wires that enter the heads-up display device 100 at a posterior end of the right earpiece 160 and connect to components within the housing 130. Other suitable configurations may be used. For example, the cable 140 may connect to an earpiece 160 of the heads-up display device 100, as shown in FIGS. 2 and 3, or may connect directly to the housing 130. The cable 140 may be positioned on a right side or a left side of the heads-up display device 100.

The cable 140 may be any type suitable to provide video information and power to the heads-up display device 100. In an exemplary embodiment, the cable 140 is a mini HDMI cable. An end of the cable 140 includes a connector 150 to allow the heads-up display device 100 to connect with a receiver 200. The connector 150 may be, for example, a female mini HDMI connector. In an exemplary embodiment, the cable 140 has a length of approximately 8 to 12 inches.

In a preferred embodiment, the housing 130 includes a printed circuit board (PCB) with components that allow for video information to be displayed. In that embodiment, the heads-up display device 100 is provided without a central processing unit (CPU), and without an operating system (OS). Thus, the heads-up display device 100 behaves as a "dumb screen" by simply displaying received video information without engaging in additional computer processes. Such an arrangement reduces display latency by eliminating extraneous processing, thereby providing an advantage over conventional heads-up display devices. Minimizing latency is critical, for example, in a surgical setting in which a live feed of a patient's vital signs must be provided to a practitioner that is delivering anesthesia. Minimizing latency allows for a decreased practitioner response time, hence minimizing emergencies. To further minimize latency, the heads-up display device 100 may be provided without audio output capability, wireless Wi-Fi connectivity, Bluetooth functionality, or a camera, features that are present in conventional heads-up display devices.

Figure 4:
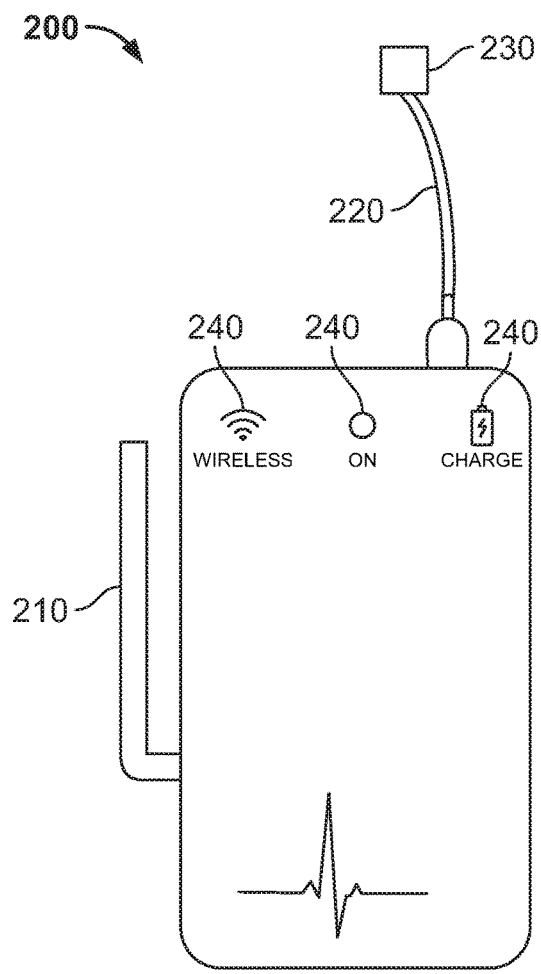
FIG. 4 shows a front view of a receiver in accordance with an embodiment of the invention.
Figure 6:
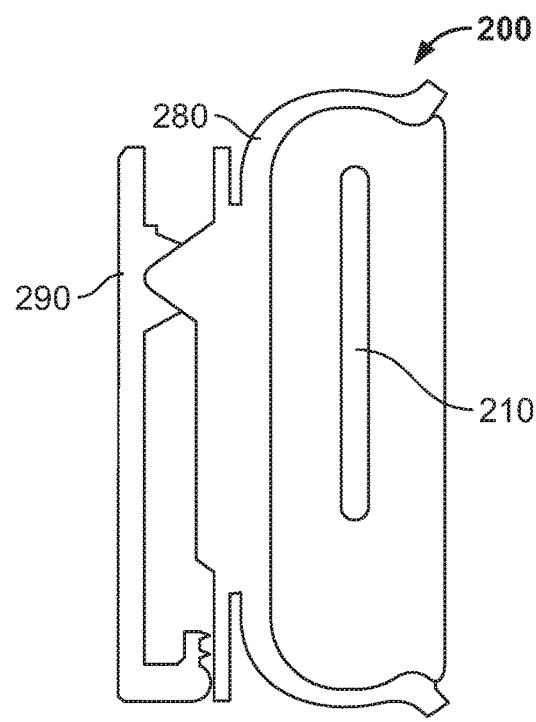
FIG. 6 shows a side view of a receiver in accordance with an embodiment of the invention.
Figure 5:
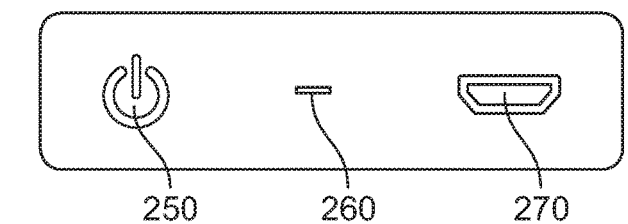
FIG. 5 shows a top view of a receiver in accordance with an embodiment of the invention.

Illustrations of an exemplary receiver 200 are provided in FIGS. 4, 5, and 6. The receiver 200 includes an antenna 210, and is configured to connect with a cable 220 having a connector 230 at its end. The receiver 200 is configured to wirelessly receive a video signal via the antenna 210 and to send video information to the heads-up display device 100.

The cable 220 may be any type suitable to provide video information and power to the heads-up display device 100. In an exemplary embodiment, the cable 220 is a mini HDMI cable. An end of the cable 220 includes a connector 230 to allow the receiver 200 to connect with the heads-up display device 100. In particular, the connector 230 of the receiver cable 220 is designed to connect with the connector 150 of the heads-up display device cable 140. The connector 230 may be, for example, a male mini HDMI connector. The cable 220 may be detachable from the receiver 200, or may be fixed to the receiver 200.

A detachable or break-away connection may be formed between the connector 230 of the receiver cable 220 and the connector 150 of the heads-up display device cable 140, such that a heads-up display device 100 may detachably connect to any compatible receiver 200, and a receiver 200 may detachably connect to any compatible heads-up display device 100. In an alternative embodiment, a single cable may be provided between the heads-up display device 100 and the receiver 200, the single cable being detachable from the heads-up display device 100, the receiver 200, or both.

The receiver 200 may include a battery, which serves as a source of power for the heads-up display device 100. In an exemplary embodiment, the battery is a built-in rechargeable battery with a capacity that will allow for at least 8 to 10 hours of working time. Alternatively, the battery may be a removable rechargeable battery. The aforementioned detachable connection between the connector 230 of the receiver cable 220 and the connector 150 of the heads-up display device cable 140 allows a user to exchange a first receiver 200 for a second receiver 200, thus allowing the battery of the first receiver 200 to charge, without the need to remove the heads-up display device 100. In an alternative embodiment, the receiver 200 may include one or more non-rechargeable replaceable batteries.

As illustrated in FIG. 4, the receiver 200 may include one or more indicators 240, which may indicate, for example, wireless signal strength, power on/off, and battery state of charge.

As illustrated in FIG. 5, the receiver 200 may include a power button 250 or switch for turning power to the receiver 200 on or off. The receiver 200 may include a port 260, such as a USB type C port, to allow the receiver 200 to connect to an external power source to charge the battery. The receiver may also include an output port 270 for detachably connecting to the cable 220, and for outputting video information and power to the heads-up display device 100. The output port 270 may be, for example, a mini HDMI output port.

The receiver 200 may be designed to be a portable unit, and may be designed to be a wearable unit. The receiver 200 may be capable of being received in a removable casing 280 with a belt clip 290 attached thereto, thus allowing the receiver 200 to be easily worn at a user's waist. In an alternative embodiment, the receiver 200 may attach directly to a belt clip 290, without a removable casing 280.

Figure 7:
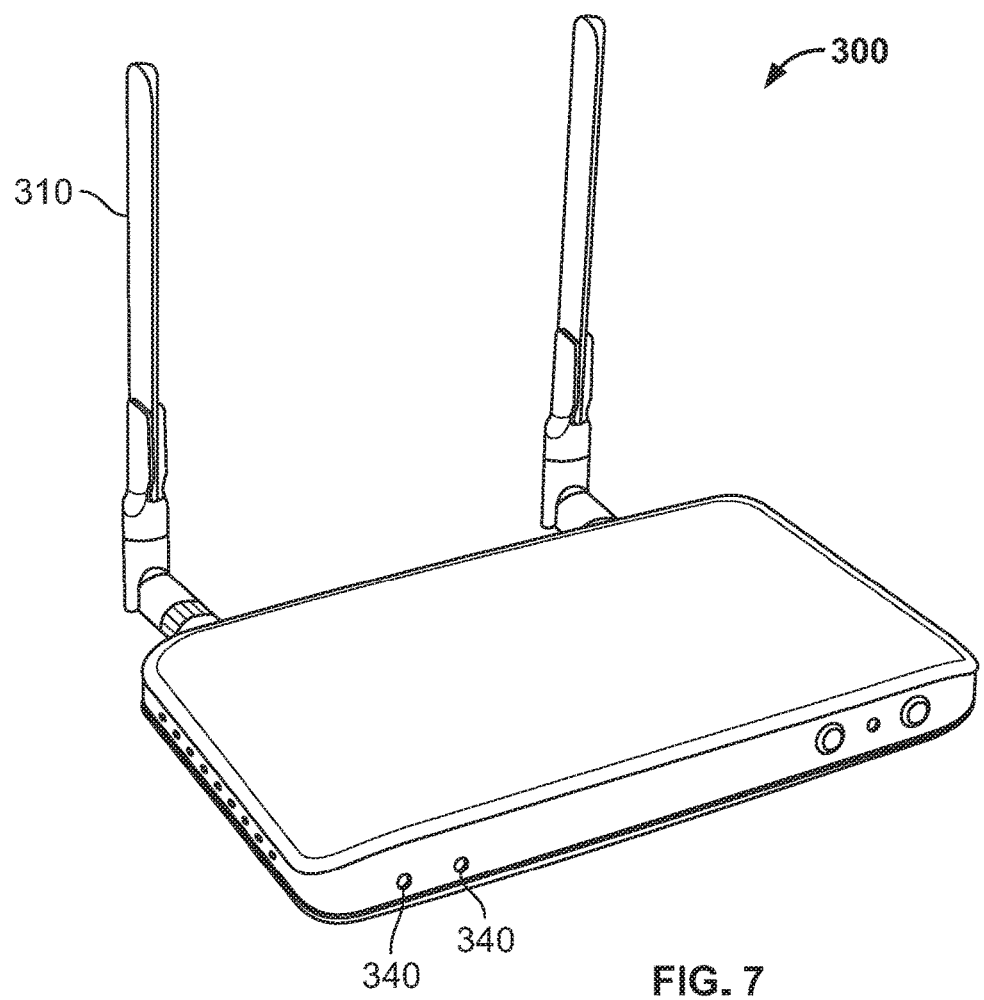
FIG. 7 shows a front perspective view of a transmitter in accordance with an embodiment of the invention.
Figure 8:
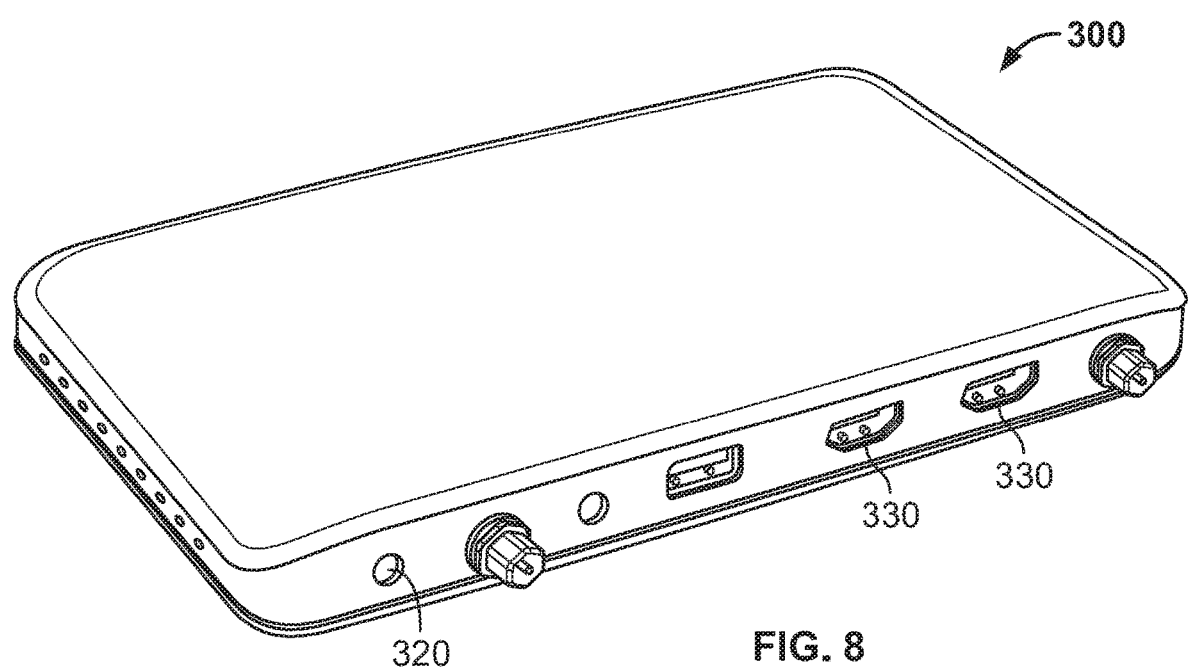
FIG. 8 shows a rear perspective view of a transmitter in accordance with an embodiment of the invention.

Illustration of an exemplary transmitter 300 are provided in FIGS. 7 and 8. The transmitter 300 includes an antenna 310, and is configured to wirelessly transmit a video signal via the antenna 310 to a receiver 200. The transmitter 300 may include a port 320 to allow the transmitter 300 to connect to an external power source, such as an AC power source. The transmitter 300 may include one or more input ports 330 via which the transmitter may receive video information from a monitor device 400 or other video source. The transmitter may include one or more indicators 340, which may indicate, for example, power on/off and whether wireless communication is enabled.

In an exemplary embodiment, the transmitter 300 may communicate with the receiver 200 via 2.5 GHz and 5.0 GHz channels. The transmitter 300 may be configured to communicate with the receiver 200 via Wi-Fi. The transmitter 300 may be configured to transmit a 780p or 1080p video signal to the receiver 200. The transmitter 300 and receiver 200 are preferably designed so as to have a latency of no more than 500 ms. The transmitter 300 and receiver 200 are preferably designed such that a line of sight is not required for successful transmission of video signals. Such a design allows a user with a heads-up display device 100 to view video information from a monitor device 400 located in different room from that of the user. While the transmitter 300 is able to transmit video signals to the receiver 200 through obstacles such as walls, such obstacles might increase latency associated with transmission, and might contribute to diminished video quality.

In an exemplary embodiment, the transmitter 330 is capable of simultaneously transmitting a video signal to multiple receivers 200, each one of the multiple receivers 200 connected to a distinct heads-up display device 100. Such capability allows multiple users to view the same video information simultaneously. Such capability is useful, for example, in an oral surgery setting in which a first user is a surgeon or anesthesiologist and a second user is a surgical or dental assistant.

The transmitter 300 may include one or more input ports 330 for receiving video information. The input ports may be, for example, HDMI ports, VGA ports, other types of video ports, or a combination thereof. For example, the transmitter 300 may include an HDMI input port and a VGA input port.

Figure 9:
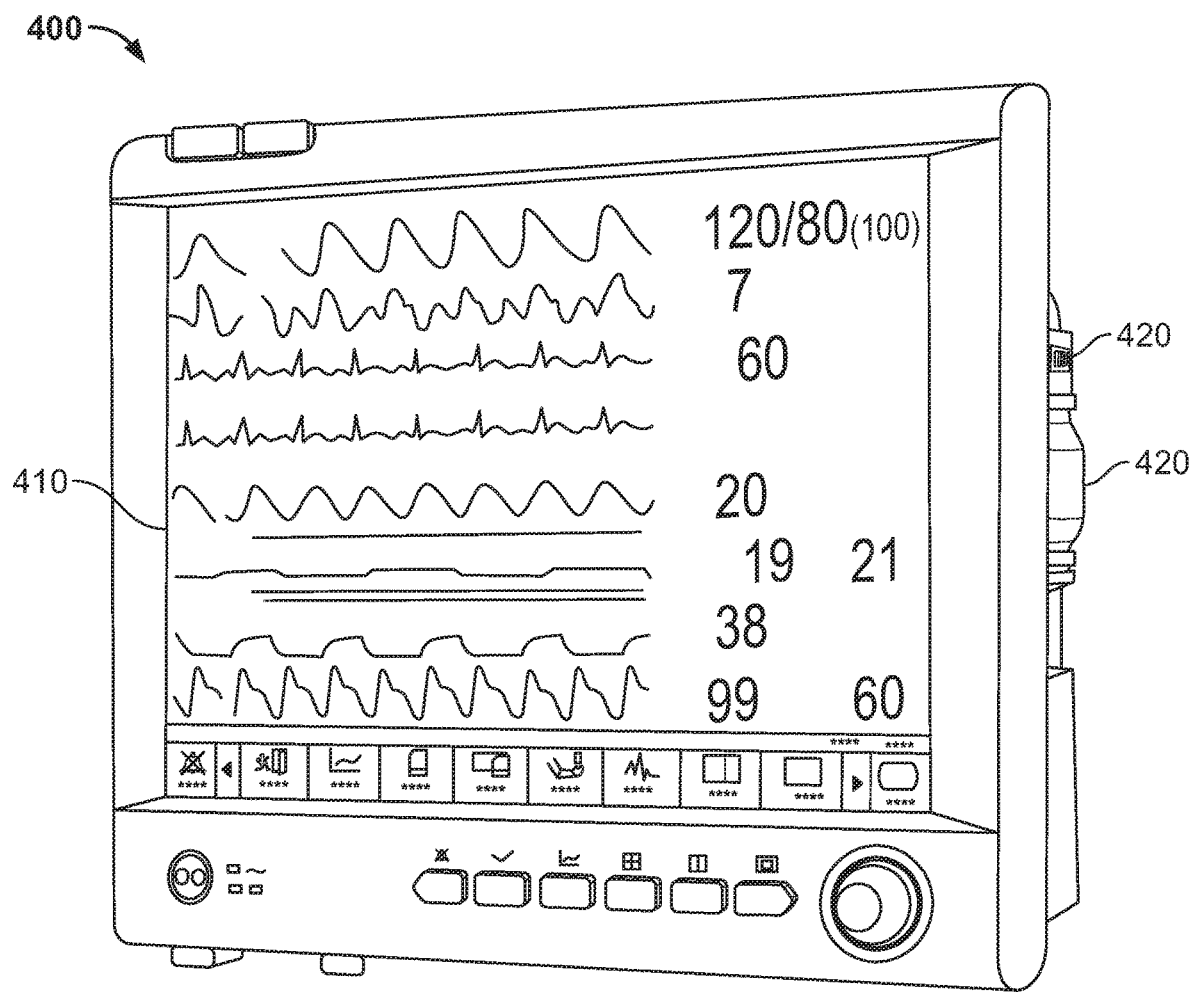
FIG. 9 shows a monitor device in accordance with an embodiment of the invention.

An illustration of an exemplary monitor device 400 is provided in FIG. 9. The monitor device 400 may be an FDA approved patient monitor device, and may be capable of monitoring, for example, blood pressure, heart rate, heart activity (electrocardiogram or EKG), respiratory activity, end tidal capnography, or pulse oximetry. The monitor device 400 may include a display 410 and one or more output ports 420, such as HDMI, VGA, or other type of video ports.

In an exemplary embodiment, the transmitter 300 connects directly to a monitor device 400 via a video cable, such as a HDMI cable or a VGA cable. In another exemplary embodiment, a converter box 500 is provided between the transmitter 300 and the monitor device 400 for converting a first type of video information to a second type of video information. A converter box 500 may prove useful in an instance in which the monitor device 400 is only capable of providing VGA video output and the transmitter 300 is only capable of receiving HDMI video input, for example. In such an instance, the converter box 500 includes a VGA input port and an HDMI output port, and converts the VGA video information from the monitor device 400 to HDMI video information to be provided to the transmitter 300. The converter box 500 may have EDID, and may be capable of converting multiple VGA resolutions and outputting 720p or 1080p video, for example.

The transmitter 300 may be a separate device as illustrated in FIGS. 7 and 8. Alternatively, the transmitter 300 may be integral to the monitor device 400 or the monitor device 400 may be configured to serve as a transmitter.

The monitoring system 10 may be configured such that the information displayed by the heads-up display device 100 is the same information displayed by the display 410 of the monitor device 400. In other words, the heads-up display device 100 mirrors the display 410 of the monitor device 400. By mirroring the display 410 instead of processing video information to display it in a format different from that of the display 410, latency within the monitoring system 10 may be reduced.

The heads-up display device 100 may be capable of displaying video information in response to voice commands. For example, a user's voice commands may cause electronic documents such as medical records, previous notes, or patient schedules to load and be displayed by the heads-up display device 100. In some embodiments, the monitoring system 10 may include a microphone, which may be located, for example, at a receiver 200 or at a heads-up display device 100. The monitoring system 10 may be configured to receive predetermined voice commands that may allow a user to navigate through a patient's medical record and imaging.

The heads-up display device 100 may be capable of displaying video information in response to gesture commands. For example, a user may make gestures, allowing the user to scroll through images displayed by the heads-up displayed device 100. Such images can include, for example, radiographic images stored on a computer. In some embodiments, the monitoring system 10 may include one or more sensors for receiving gesture input from a user. Sensors may be located, for example, at a receiver 200 or at a heads-up display device 100. The monitoring system 10 may be configured to receive predetermined voice commands that may allow a user to navigate through a patient's medical record and imaging. The monitoring system 10 may be configured to respond to gestures such as scroll gestures and swipe gestures, allowing a user to manipulate the display of information on the heads-up display device 100. The ability of the monitoring system 10 to respond to gesture controls enhances a user's ability to maintain a clean and sterile work environment, as gesture controls offer a hands-free approach to manipulating a display. Gesture controls, and voice controls, may be processed by a CPU that is provided in an pathway that is independent from that of live vital sign monitoring, so as not to increase latency during the transmission of live vital sign information to be displayed.

Figure 10:
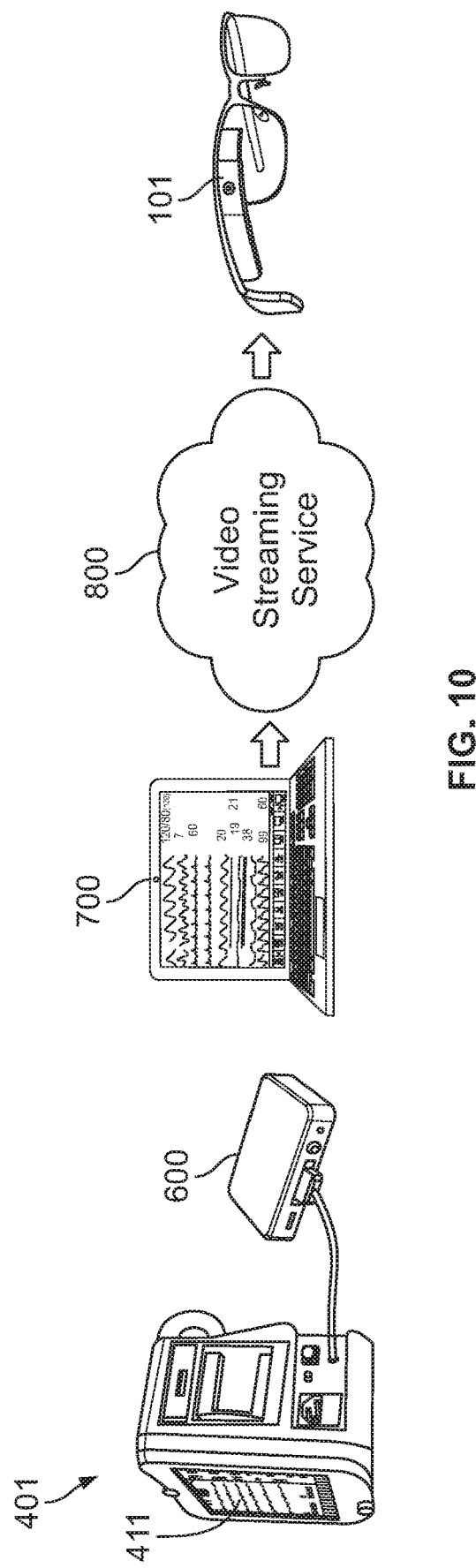
FIG. 10 shows a monitoring system in accordance with another embodiment of the invention.

FIG. 10 shows an alternative exemplary embodiment of a monitoring system 20 in accordance with the invention. As shown in FIG. 10, a monitor device 401 may include a display 411, and may connect to a screen capturing device 600 that serves as a transmission device. The screen capturing device 600 may be a separate device as illustrated in FIG. 10. Alternatively, the screen capturing device 600 may be integral to the monitor device 401 or the monitor device 401 may be configured to serve as a screen capturing device. The screen capturing device 600 captures real-time or periodic snapshot video information or other data from the monitor device 401 and transmits that video information or other data to a computer 700 or other electronic device. The computer 700 may then stream the video information or other data to a heads-up display device 101 by way of, for example, a video streaming service 800. In this and other exemplary embodiments, periodic snapshot video information may be captured at set intervals (e.g., 30 seconds, 1 minute, 5 minutes), and may be stored for later retrieval by a user. Storage of snapshot video information may, for example, assist a healthcare provider in satisfying documentation requirements for insurance or other purposes.

Figure 11:
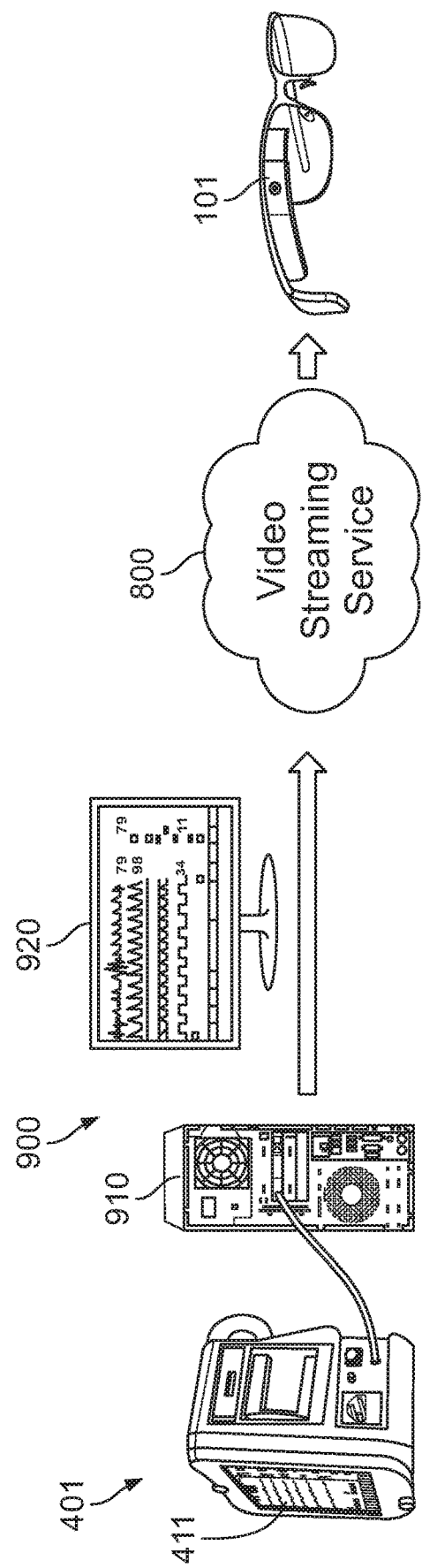
FIG. 11 shows a monitoring system in accordance with another embodiment of the invention.

FIG. 11 shows an alternative exemplary embodiment of a monitoring system 30 in accordance with the invention. As shown in FIG. 11, a monitor device 401 may include a display 411, and may connect to a computer 900 that serves as a screen capturing device and a transmission device. The computer 900 may include a CPU 910 and a display 920. The computer display 920 may be configured to mirror video information from the monitor device display 411, either in real-time or by way of periodic snapshots. The computer 900 may transmit video information or other data from the monitor device 401 or from the computer 900 to a heads-up display device 101 by way of, for example, a video streaming service 800.

Figure 12:
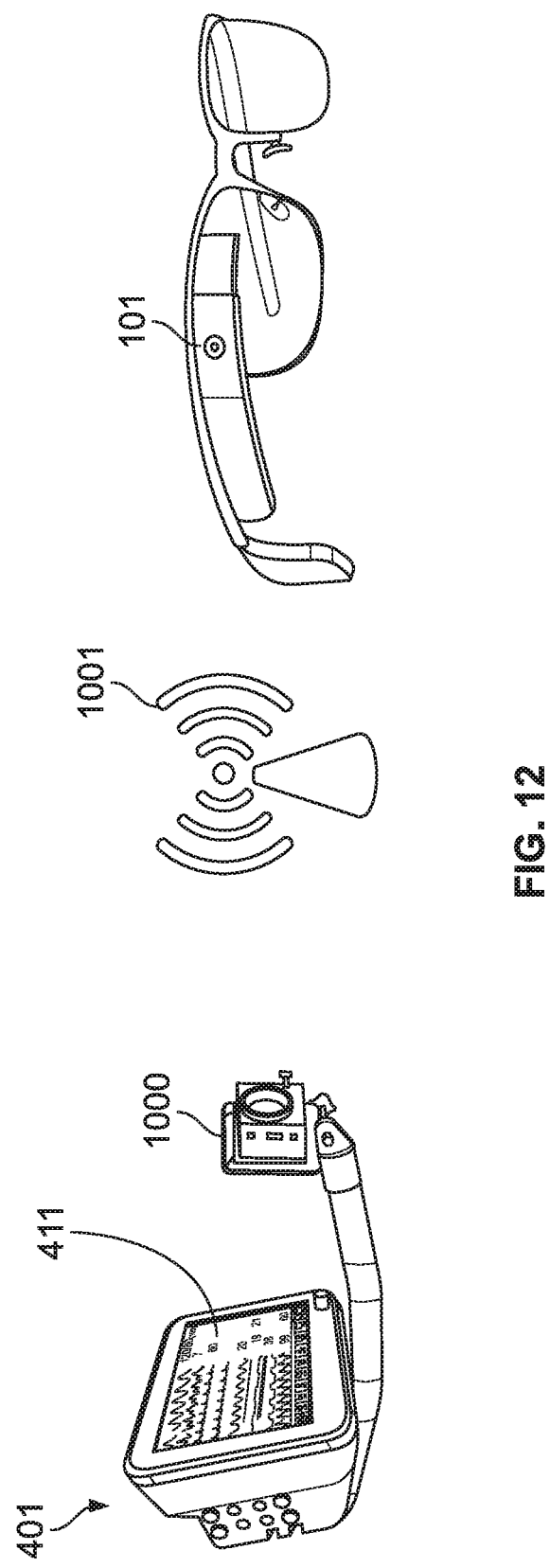
FIG. 12 shows a monitoring system in accordance with another embodiment of the invention.

FIG. 12 shows an alternative exemplary embodiment of a monitoring system 40 in accordance with the invention. As shown in FIG. 12, a monitor device 401 may include a display 411, and may have a camera 1000 mounted thereon, the camera 1000 serving as a transmission device. The camera 1000 may be, for example, any type of digital camera that is capable of capturing and transmitting video information. The camera 1000 may be, for example, a mobile phone camera. The camera 1000 captures real-time or periodic snapshot video information from the monitor device 401, and may transmit that video information to a heads-up display device 101 via a wireless connection 1001, such as a Wi-Fi or Bluetooth connection.

Figure 13:
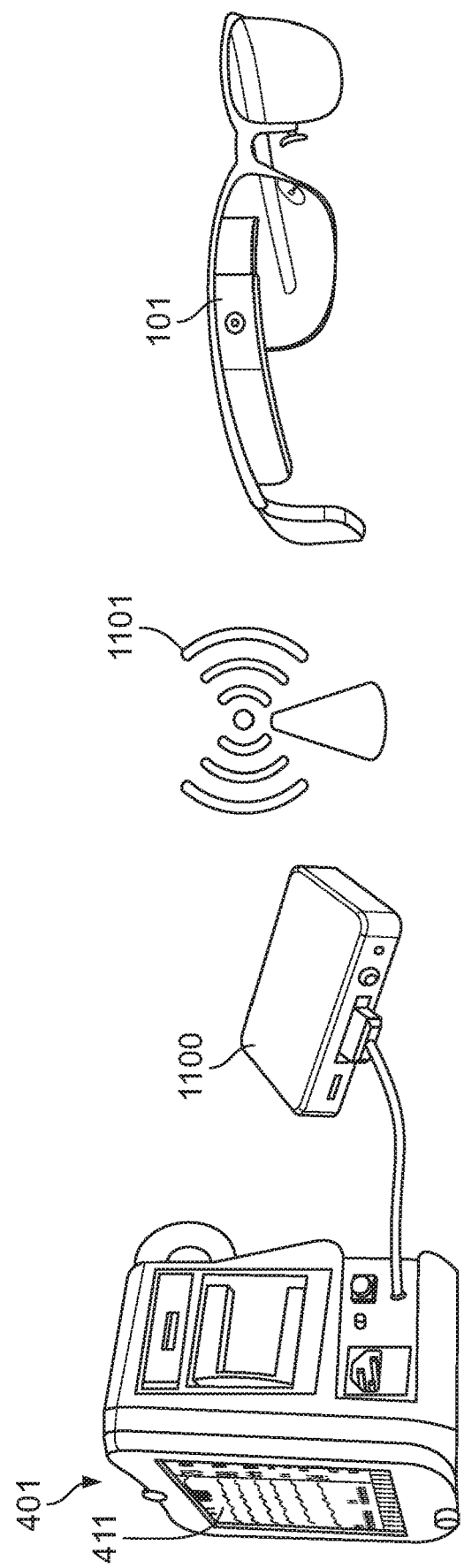
FIG. 13 shows a monitoring system in accordance with another embodiment of the invention.

FIG. 13 shows an alternative exemplary embodiment of a monitoring system 50 in accordance with the invention. As shown in FIG. 13, a monitor device 401 may include a display 411, and may connect to an external box 1100 that serves as a transmission device. The external box 1100 captures real-time or periodic snapshot video information, or other data, from the monitor device 401, and may transmit that video information or other data to a heads-up display device 101 via a wireless connection 1101, such as a Wi-Fi or Bluetooth connection. The external box 1100 may connect to the monitor device 401 via any suitable type of video or data connection, such as VGA, DVI, HDMI, DisplayPort, or Ethernet.

To account for Health Insurance Portability and Accountability Act (HIPPA) considerations, as well as the fact that (i) most networked hospital patient monitor devices are homogenous in brand to ensure compatibility and (ii) available display ports vary from model to model, various implementations of the invention are contemplated. Further, it is recognized in the design that the type of data from Ethernet ports may be proprietary or even encrypted to prevent stolen data, and that some hospitals keep their networks offline to prevent hacking.

While the invention may be particularly useful in medical applications, as described herein, the invention may be of use in other applications and is therefore not limited to a particular application.

It should be recognized that certain components or elements of the embodiments described above, or in the claims that follow, are numbered to allow ease of reference to them or to help distinguish between them, but order should not be implied from such numbering, unless such order is expressly recited. The above description and drawings are only to be considered illustrative of specific embodiments, which achieve the features and advantages described herein. Accordingly, the embodiments in this patent document are not considered as being limited by the foregoing description and drawings.

What is claimed is:

1. A monitoring system comprising:
   a heads-up display device;
   a receiver;
   a cable connecting the receiver to the heads-up display device; and
   a transmitter configured to wirelessly transmit a video signal to the receiver,
   wherein the receiver is configured to receive the video signal and to provide video information to the heads-up display device via the cable,
   wherein the receiver includes a battery, and is configured to supply power to the heads-up display device via the cable,
   wherein the receiver is configured to detach from the heads-up display device,
   wherein the heads-up display device does not include a battery, and
   wherein the heads-up display device does not include a CPU or an operating system.

2. The monitoring system of claim 1, wherein the receiver is configured to provide HDMI video information to the display device.

3. The monitoring system of claim 1, wherein the receiver is a wearable receiver.

4. The monitoring system of claim 1, wherein the transmitter is configured to receive VGA video information and HDMI video information.

5. The monitoring system of claim 1 further comprising a monitor device configured to provide video information to the transmitter.

6. The monitoring system of claim 5, wherein the monitor device includes at least one of a blood pressure monitor, a heart rate monitor, an electrocardiograph, a respiratory monitor, a capnograph, and a pulse oximeter.

7. The monitoring system of claim 5 further comprising a converter configured to convert video information from the monitor device to HDMI format.

8. The monitoring system of claim 1 further comprising:
   a second heads-up display device; and
   a second receiver configured to receive the video signal and to provide video information to the second heads-up display device.

9. The monitoring system of claim 1, wherein the heads-up display device includes at least one safety lens.

10. The monitoring system of claim 1, wherein the heads-up display device includes an LCOS (liquid crystal on silicon) display.

11. The monitoring system of claim 1, wherein the heads-up display device includes a brightness controller.

12. The monitoring system of claim 1, wherein the heads-up display device is configured to display information only in a peripheral field.

13. The monitoring system of claim 1, wherein the heads-up display device is configured to display information in response to voice commands.

14. The monitoring system of claim 1, wherein the heads-up display device is configured to display information in response to gesture commands.

* * * * *